US00PP16779P2

(12) United States Plant Patent
Tanaka et al.

(10) Patent No.: US PP16,779 P2
(45) Date of Patent: Jul. 11, 2006

(54) ***FUCHSIA* PLANT NAMED 'SANIHANF ARL2'**

(50) Latin Name: *Fuchsia×hybrida*
Varietal Denomination: Sanihanf arl2

(75) Inventors: Toshi Tanaka, Hyogo (JP); Hidefumi Funakoshi, Hyogo (JP); Mito Ikeda, Hyogo (JP); Yasuyuki Murakami, Shiga (JP)

(73) Assignees: Nishinomiya City, Hyogo (JP); Suntory Flowers Ltd., Tokyo (JP)

( * ) Notice: Subject to any disclaimer, the term of this patent is extended or adjusted under 35 U.S.C. 154(b) by 55 days.

(21) Appl. No.: 11/055,826

(22) Filed: Feb. 11, 2005

(51) Int. Cl.
*A01H 5/00* (2006.01)

(52) U.S. Cl. ..... Plt./300

(58) Field of Classification Search ..... Plt./300
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Fuchsia* plant named 'Sanihanf arl2', characterized by its compact and cascading growth habit; freely branching habit; dense and bushy plant habit; red purple and white-colored flowers; freely and continuous flowering habit; and relative tolerance to high temperatures.

1 Drawing Sheet

Botanical denomination: *Fuchsia×hybrida.*
Cultivar denomination: 'Sanihanf arl2'.

BACKGROUND OF THE INVENTION

The present invention relates to a new and distinct cultivar of *Fuchsia* plant, botanically known as *Fuchsia×hybrida*, and hereinafter referred to by the name 'Sanihanf arl2'.

The new *Fuchsia* is a product of a planned breeding program conducted by the Inventors in Hyogo, Japan. The objective of the breeding program was to create new *Fuchsia* cultivars with a compact and bushy plant habit, numerous attractive flowers and tolerance to high temperatures.

The new *Fuchsia* originated from a cross-pollination made by the Inventors in 2000 of a proprietary selection *Fuchsia×hybrida* identified as code number aip-18, not patented, as the female, or seed, parent with the *Fuchsia×hybrida* cultivar Hidcote Beauty, not patented, as the male, or pollen, parent. The cultivar Sanihanf arl2 was discovered and selected by the Inventors as a flowering plant within the resulting progeny of the stated cross-pollination in a controlled environment in Hyogo, Japan.

Asexual reproduction of the new *Fuchsia* by terminal cuttings in Shiga, Japan, since May, 2002 has shown that the unique features of this new *Fuchsia* are stable and reproduced true to type in successive generations.

BRIEF SUMMARY OF THE INVENTION

The cultivar Sanihanf arl2 has not been observed under all possible environmental conditions. The phenotype may vary somewhat with variations in environment such as temperature and daylength, without, however, any variance in genotype.

The following traits have been repeatedly observed and are determined to be the unique characteristics of 'Sanihanf arl2'. These characteristics in combination distinguish 'Sanihanf arl2' as a new and distinct *Fuchsia* cultivar:

1. Compact and cascading growth habit.
2. Freely branching habit; dense and bushy plant habit.

3. Red purple and white-colored flowers.
4. Freely and continuous flowering habit.
5. Relatively tolerant to high temperatures.

Plants of the new *Fuchsia* can be compared to plants of the female parent selection. In side-by-side comparisons conducted in Hyogo and Shiga, Japan, plants of the new *Fuchsia* differed from plants of the female parent selection in the following characteristics:

1. Plants of the new *Fuchsia* had flatter leaves than plants of the female parent selection.
2. Plants of the new *Fuchsia* had single flowers whereas plants of the female parent selection had semi-double and double flowers.
3. Plants of the new *Fuchsia* has longer calyx tubes than plants of the female parent selection.
4. Plants of the new *Fuchsia* and the female parent selection differed in corolla and calyx coloration.

Plants of the new *Fuchsia* can be compared to plants of the male parent, the cultivar Hidcote Beauty. In side-by-side comparisons conducted in Hyogo and Shiga, Japan, plants of the new *Fuchsia* differed from plants of the cultivar Hidcote Beauty in the following characteristics:

1. Plants of the new *Fuchsia* had narrower leaves than plants of the cultivar Hidcote Beauty.
2. Plants of the new *Fuchsia* had shorter flowers than plants of the cultivar Hidcote Beauty.
3. Plants of the new *Fuchsia* and the cultivar Hidcote Beauty differed in corolla coloration.

Plants of the new *Fuchsia* can also be compared to plants of the cultivar Sanihanf, disclosed in U.S. Plant Pat. No. 10,378. In side-by-side comparisons conducted in Hyogo and Shiga, Japan, plants of the new *Fuchsia* differed from plants of the cultivar Sanihanf in the following characteristics:

1. Plants of the new *Fuchsia* had larger leaves with longer petioles than plants of the cultivar Sanihanf.
2. Plants of the new *Fuchsia* had longer calyx tubes than plants of the cultivar Sanihanf.

3. Plants of the new *Fuchsia* and the cultivar Sanihanf differed in stem, leaf petiole, corolla and calyx coloration.

BRIEF DESCRIPTION OF THE PHOTOGRAPHS

The accompanying colored photographs illustrate the overall appearance of the new *Fuchsia*, showing the colors as true as it is reasonably possible to obtain in colored reproductions of this type. Colors in the photographs may differ slightly from the color values cited in the detailed botanical description which accurately describe the colors of the new *Fuchsia*.

The photograph at the top of the sheet comprises a side perspective view of a typical potted plant of 'Sanihanf arl2'.

The photograph at the bottom sheet is a close-up view of typical flowers of 'Sanihanf arl2'.

DETAILED BOTANICAL DESCRIPTION

The aforementioned photographs and following observations and measurements describe plants grown in Hyogo, Japan, under commercial practice in a polyethylene-covered greenhouse with day and night temperatures averaging 25 and 15° C., respectively. One cutting was planted per 13.5-cm container and plants were grown for about twelve months. In the following description, color references are made to The Royal Horticultural Society Colour Chart, 2001 Edition, except where general terms of ordinary dictionary significance are used.

Botanical classification: *Fuchsia×hybrida* cultivar Sanihanf arl2.

Parentage:

*Female or seed parent*.—Proprietary selection of *Fuchsia×hybrida* identified as code number aip-18, not patented.

*Male, or pollen, parent*.—*Fuchsia×hybrida* cultivar Hidcote Beauty, not patented.

Propagation:

*Type cutting*.—Terminal cuttings.

*Time to initiate roots*.—About one week at 20° C.

*Time to produce a rooted cutting*.—About three weeks at 20° C.

*Root description*.—Fine, fibrous, fleshy; yellowish white in color.

*Rooting habit*.—Freely-branching.

Plant description:

*Form and habit*.—Compact and cascading growth habit; freely branching habit, dense and bushy plant habit; pinching (removal of terminal apex) enhances lateral branch development; freely flowering habit; vigorous.

*Plant height at flowering*.—About 30 cm.

*Plant diameter at flowering*.—About 30 cm.

*Lateral branch description*.—Length: About 20 cm. Diameter: About 2.3 mm. Internode length: About 2.2 cm. Strength: Strong. Texture: Pubescent. Color: Close to 144A.

*Foliage description*.—Arrangement: Opposite, simple. Length: About 6.1 cm. Width: About 3.4 cm. Shape: Elliptic. Apex: Acute. Base: Obtuse. Margin: Entire. Texture, upper and lower surfaces: Slightly pubescent towards the margins. Venation pattern: Pinnate, reticulate. Petiole length: About 1.3 cm. Petiole diameter: About 1.7 mm. Petiole texture, upper and lower surfaces: Smooth, glabrous. Color: Developing and fully expanded leaves, upper surface: 137A; venation, similar to lamina. Developing and fully expanded leaves, lower surface: 138B; venation, similar to lamina. Petiole, upper and lower surfaces: 145A.

Flower description:

*Flower type and habit*.—Single bi-colored axillary flowers. Freely flowering; potentially two flowers per leaf axil. Flowers not persistent. Flowers not fragrant.

*Natural flowering season*.—Spring to autumn in Japan; flowering continuous during this period.

*Flower longevity*.—Flowers last about three to four days on the plant.

*Flower orientation*.—Initially upright, then pendulous.

*Flower diameter*.—About 4.3 cm.

*Flower length*.—About 3.4 cm.

*Flower buds*.—Shape: Elongated. Length: About 3.7 cm. Width: About 1.1 cm. Color: N155B.

*Petals*.—Quantity: Four; imbricate; in a single whorl. Length: About 1.8 cm. Width: About 1.6 cm. Shape: Broadly obovate. Apex: Truncate. Base: Rounded. Margin: Entire. Texture, upper and lower surfaces: Glabrous, smooth and satiny. Color: When opening, upper and lower surfaces: 77A; venation, N74C. Fully opened, upper and lower surfaces: N78A; venation, N74C.

*Sepals*.—Quantity: Four; fused at base. Length: About 3.1 cm. Width: About 9 mm. Calyx tube length: About 1.5 cm. Calyx tube diameter: About 5 mm. Shape: Lanceolate. Apex: Acute. Base: Obtuse. Margin: Entire. Texture, upper and lower surfaces: Glabrous, smooth. Color: When opening, upper and lower surfaces: N155B. Fully opened, upper and lower surfaces: N155B.

*Peduncles*.—Length: About 4.8 cm. Diameter: About 0.9 mm. Strength: Moderately strong. Texture: Pubescent. Color: 145B.

*Reproductive organs*.—Stamens: Stamen number: Eight per flower. Anther size: About 3.8 mm by 1.9 mm. Anther shape: Ellipsoidal. Anther color: 68C. Pollen amount: Moderate. Pollen color: 68A. Pistils: Pistil nunber: One per flower. Pistil length: About 5.3 cm. Style length: About 1.9 cm. Style color: 68C. Stigma shape: Ellipsoidal. Stigma color: 10A. Ovary color: 144A.

*Seed/fruit*.—Seed and fruit production has not been observed.

Disease/pest resistance: Plants of the new *Fuchsia* have not been observed to be resistant to pathogens and pests common to *Fuchsias*.

Temperature tolerance: Plants of the new *Fuchsia* have been observed to tolerate low temperatures of 3° C. and high temperatures of 35° C. Compared to other *Fuchsia* cultivars known to the Inventors, plants of the new *Fuchsia* are relatively tolerant to high temperatures.

Garden performance: Plants of the new *Fuchsia* perform have been observed to perform well in the garden and are tolerant to rain and wind.

It is claimed:

1. A new and distinct cultivar of *Fuchsia* plant named 'Sanihanf arl2', as illustrated and described.

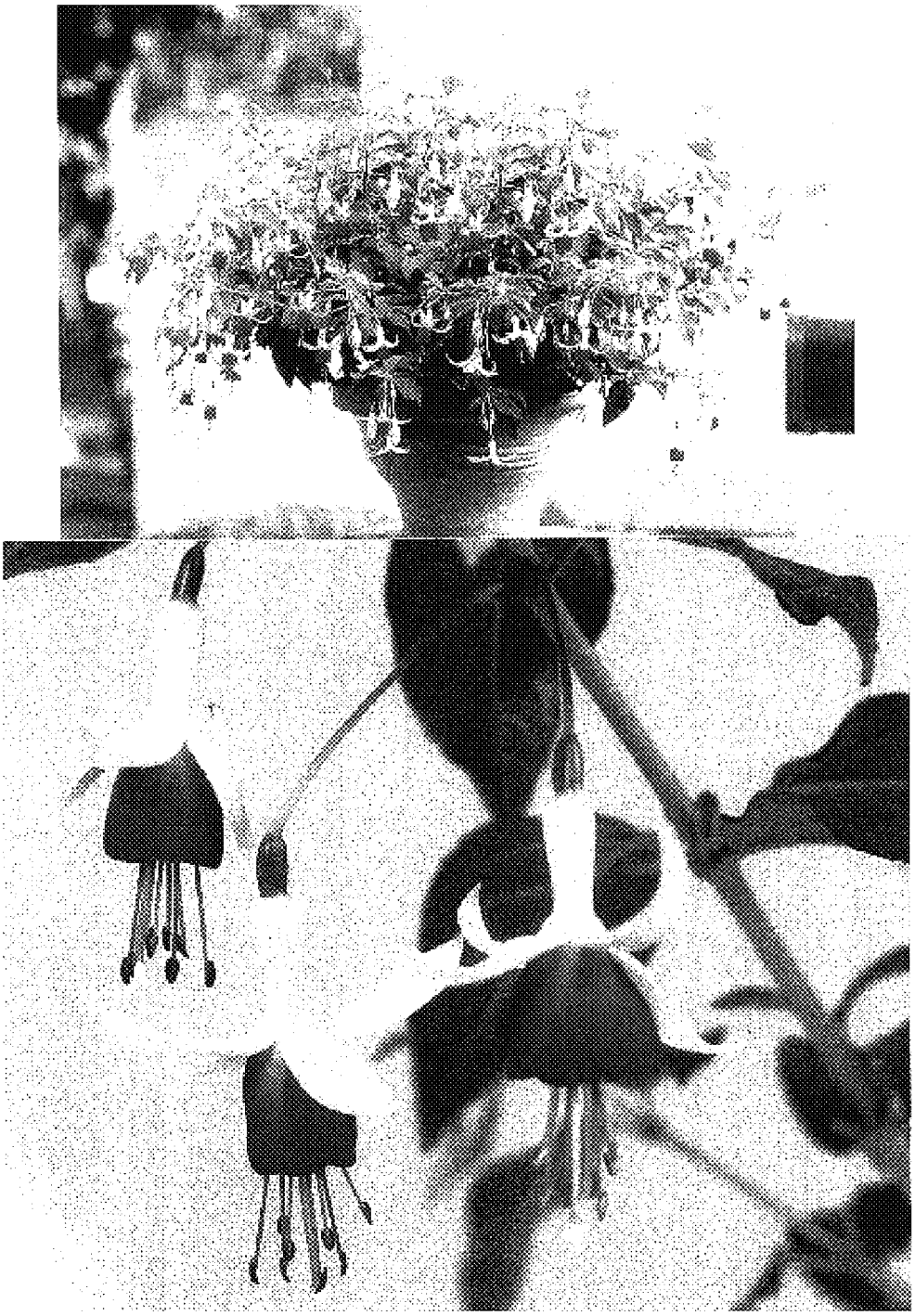

* * * * *